(12) United States Patent
Bartmann et al.

(10) Patent No.: US 6,573,404 B2
(45) Date of Patent: Jun. 3, 2003

(54) METHOD FOR PRODUCING ORTHO-ALKYLATED BENZOIC ACID DERIVATIVES

(75) Inventors: Ekkehard Bartmann, Erzhausen (DE); Ingeborg Stein, Rodgau (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/265,607

(22) Filed: Oct. 8, 2002

(65) Prior Publication Data

US 2003/0069444 A1 Apr. 10, 2003

Related U.S. Application Data

(62) Division of application No. 10/038,602, filed on Jan. 8, 2002, and a division of application No. 09/744,302, filed on Apr. 5, 2001, now Pat. No. 6,350,904.

(30) Foreign Application Priority Data

Jul. 23, 1998 (DE) .......................................... 198 33 118

(51) Int. Cl.[7] .............................................. C07C 279/22
(52) U.S. Cl. ....................... 564/162; 564/237; 562/405; 570/101
(58) Field of Search ................................ 564/162, 237; 562/405; 570/101

(56) References Cited

U.S. PATENT DOCUMENTS 5,807,896 A * 9/1998 Gericke et al. ............... 514/18

* cited by examiner

Primary Examiner—Ceila Chang
Assistant Examiner—Kamal Saeed
(74) Attorney, Agent, or Firm—Millen, White, Zelano & Branigan, P.C.

(57) ABSTRACT

The invention relates to a process for the preparation of ortho-alkylated benzoic acid derivatives of the formula I

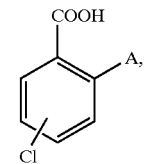

characterized in that an aryl bromide of the formula II

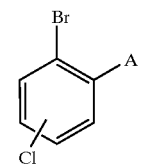

is reacted with a secondary or tertiary organolithium compound and $CO_2$.

3 Claims, No Drawings

METHOD FOR PRODUCING ORTHO-ALKYLATED BENZOIC ACID DERIVATIVES

This application is a divisional of application Ser. No. 10/038,602 filed Jan. 8, 2002 which is a divisional of application Ser. No. 09/744,302 filed Apr. 5, 2001 now U.S. Pat. No. 6,350,904.

The invention relates to a process for the preparation of ortho-alkylated benzoic acid derivatives of the formula I

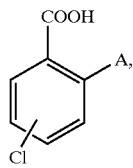

in which

A is an alkyl radical having from 1 to 4 carbon atoms, characterized in that an aryl bromide of the formula II

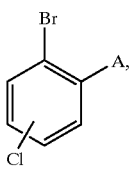

in which A is as defined in formula I,
is reacted with a secondary or tertiary organolithium compound and $CO_2$.

Ortho-alkylated benzoic acid derivatives of the formula I are important intermediates in industrial organic synthesis, e.g. in the preparation of fine chemicals, dyes and crop-protection compositions. They are also important intermediates in the preparation of medicaments, in particular in the preparation of inhibitors of the cellular $Na^+/H^+$ antiporter, which are known from EP 0 699 666 A1 or EP 0 758 644. In particular, 4-chloro-2-methylbenzoic acid is an intermediate in the synthesis of N-diaminomethylene-2-methyl -4-(1-pyrrolyl)-5-methylsulfonylbenzamide, known from EP 0 699 666 A1 or N-diaminomethylene-2-methyl-4,5-di (methylsulfonyl)benzamide, known from EP 0 758 644.

From classical organic synthesis (see on this subject standard works on organic synthesis, such as Houben-Weyl, Methoden der organischen Chemie [Methods in Organic Chemistry], Georg-Thieme-Verlag, Stuttgart, or Beyer, Walter, Lehrbuch der organischen Synthese [Handbook of Organic Synthesis], S. Hirzel Verlag, Stuttgart), the preparation of ortho-alkylated benzoic acid derivatives from aniline derivatives by diazotization, Sandmeyer reaction and subsequent nitrile hydrolysis, or by ortho-metalation and subsequent alkylation of benzoic acid derivatives, is known. For economic and ecological reasons, these multistage synthesis sequences are unpracticable for industrial application.

H. Gilman et al., J. Am. Chem. Soc. 1940, 62, 2327f. describes the synthesis of benzoic acid derivatives by lithiation of the corresponding aryl bromides and subsequent carboxylation. The preparation of 2-methyl-benzoic acid by reaction of o-bromotoluene with n-butyllithium and subsequent carboxylation with solid $CO_2$ achieves a yield of 83.8%. The reaction of 4-chlorobromobenzene with n-butyllithium and $CO_2$ gives 4-chlorobenzoic acid with a 90% yield.

Preparation of the ortho-alkylated compounds of the formula I, in particular of 4-chloro-2-methylbenzoic acid, is impossible using the synthesis described above. Under the reaction conditions described in H. Gilman et al., J. Am. Chem. Soc. 1940, 62, 2327f., and using the customary lithiation reagents n-butyllithium, n-hexyllithium, phenyllithium or methyllithium, the desired reaction does not take place at all or only with a very low yield.

These findings are further supported by the synthesis of 4-chloro-2-methylbenzoic acid which is described in U.S. Pat. No. 3,910,947. Firstly, 2-methyl-4-chloroaniline is diazotized and the diazonium salt is scavenged with KI to synthesize the very reactive 2-iodo-4-chlorotoluene, which is immediately converted into 4-chloro-2-methylbenzoic acid by reaction with n-butyllithium and $CO_2$. The choice of the very reactive aryl iodide over the less expensive and more readily available bromine derivative confirms that it was hitherto impossible to convert the aryl bromides into the desired benzoic acid derivatives of the formula I in a satisfactory yield.

The object of the invention was therefore to develop a process for the preparation of ortho-alkylated benzoic acid derivatives of the formula I which permits the use of aryl bromides.

Surprisingly, it has been found that the reaction of the aryl bromides of the formula II with a secondary or tertiary organolithium compound as metalation agent takes place with a yield which is improved compared with the prior art or is very good.

As a result, we have provided a way of preparing the ortho-alkylated benzoic acid derivatives of the formula I by a reaction, which is easy to handle even on an industrial scale, as a one-pot synthesis under mild conditions and using bromine derivatives of the formula II, which are less expensive than the aryl iodides.

The invention therefore provides a process for the preparation of ortho-alkylated benzoic acid derivatives of the formula I

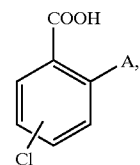

characterized in that an aryl bromide of the formula II

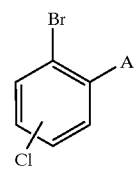

is reacted with a secondary or tertiary organolithium compound and $CO_2$.

The invention further provides a process for the preparation of ortho-alkylated benzoic acids of the formula I, characterized in that a secondary organolithium compound chosen from the group consisting of sec-butyllithium, isopropyllithium, sec-amyllithium, 4-heptyllithium, cyclopropyllithium or cyclohexyllithium or a tertiary organolithium compound chosen from the group consisting of tert-butyllithium, tert-amyllithium, triethylmethyllithium, 1-methylcyclopentyllithium or adamantyllithium is used.

The invention further provides a process for the preparation of ortho-alkylated benzoic acid derivatives of the formula I, characterized in that the reaction is carried out at temperatures between −100° and +50° C., and the reaction product is precipitated by adding an acid.

The invention further provides a process for the preparation of ortho-alkylated benzoic acid derivatives of the formula I, characterized in that the reaction is carried out in an inert solvent chosen from the group consisting of diethyl ether, methyl tert-butyl ether, tetrahydrofuran, dioxane, toluene, hexane, petroleum ether or mixtures thereof.

The invention further provides a process for the preparation of ortho-alkylated benzoic acid derivatives of the formula I, characterized in that the aryl bromide of the formula II is introduced into an inert solvent, the secondary or tertiary organolithium compound is added, this reaction mixture is added dropwise to a $CO_2$-saturated solvent, and the mixture is again saturated with $CO_2$.

The invention preferably provides a process for the preparation of 4-chloro-2-methylbenzoic acid, characterized in that 2-bromo-5-chlorotoluene is reacted with a secondary or tertiary organolithium compound and $CO_2$.

The invention particularly preferably provides a process for the preparation of 4-chloro-2-methylbenzoic acid, characterized in that a) 2-bromo-5-chlorotoluene is reacted with sec-butyllithium and $CO_2$, b) the reaction is carried out at temperatures between −100° and +50° C., and 4-chloro-2-methylbenzoic acid is precipitated by adding an acid, c) the reaction is carried out in an inert solvent chosen from the group consisting of diethyl ether, methyl tert-butyl ether, tetrahydrofuran, dioxane, toluene, hexane, petroleum ether or mixtures thereof, and d) the 2-bromo-5-chlorotoluene is introduced into an inert solvent, the sec-butyllithium is added, this reaction mixture is added dropwise to a $CO_2$-saturated solvent, and the mixture is again saturated with $CO_2$.

The invention further provides for the use of 4-chloro-2-methylbenzoic acid prepared from the process described above as intermediate in the synthesis of N-diaminomethylene-2-methyl-4-(1-pyrrolyl)-5-methylsulfonylbenzamide.

The invention also provides a process for the preparation of N-diaminomethylene-2-methyl-4-(1-pyrrolyl)-5-methylsulfonylbenzamide characterized in that in stage a) 2-bromo-5-chlorotoluene is reacted with a secondary or tertiary organolithium compound, particularly preferably sec-butyllithium, and $CO_2$ to give 4-chloro-2-methylbenzoic acid, in stage b) 4-chloro-2-methylbenzoic acid is reacted with chlorosulfonic acid, sodium sulfite and methyl iodide to give 2-methyl-4-chloro-5-methylsulfonylbenzoic acid, in stage c) 2-methyl-4-chloro-5-methylsulfonylbenzoic acid is reacted with benzylamine to give 4-benzylamino-5-methylsulfonyl-2-methylbenzoic acid, in stage d) 4-benzylamino-5-methylsulfonyl-2-methylbenzoic acid is esterified with an alcohol to give the corresponding ester of 4-benzylamino-5-methylsulfonyl-2-methylbenzoic acid, in stage e) the ester from stage d) is reduced to give the corresponding 4-amino-5-methylsulfonyl-2-methylbenzoic ester, in stage f) 4-amino-5-methylsulfonyl-2-methylbenzoic ester is reacted with dimethoxytetrahydrofuran to give 2-methyl-4-(1-pyrrolyl)-5-methylsulfonylbenzoic ester, and in stage g) 2-methyl-4-(1-pyrrolyl)-5-methylsulfonylbenzoic ester is reacted with guanidine to give N-diaminomethylene-2-methyl-4-(1-pyrrolyl)-5-methylsulfonylbenzamide.

In stage d) preference is given to using an aliphatic alcohol having from 1 to 6 carbon atoms, such as, for example, methanol, ethanol, propanol, butanol, pentanol or hexanol. Particular preference is given to using methanol.

The invention further provides for the use of 4-chloro-2-methylbenzoic acid, prepared from the process described above, as intermediate in the synthesis of N-diaminomethylene-2-methyl-4,5-di(methylsulfonyl)benzamide.

The invention also provides a process for the preparation of N-diaminomethylene-2-methyl-4,5-di(methylsulfonyl)benzamide, characterized in that in stage a) 2-bromo-5-chlorotoluene is reacted with a secondary or tertiary organolithium compound, particularly preferably sec-butyllithium, and $CO_2$ to give 4-chloro-2-methylbenzoic acid, in stage b) 4-chloro-2-methylbenzoic acid is reacted with chlorosulfonic acid, sodium sulfite and methyl iodide to give 2-methyl-4-chloro-5-methylsulfonylbenzoic acid, in stage c) 2-methyl-4-chloro-5-methylsulfonylbenzoic acid is reacted with sodium methylthiolate and then oxidized with an oxidizing agent to give 2-methyl-4,5-di (methylsulfonyl)benzoic acid, in stage d) 2-methyl-4,5-di(methylsulfonyl)benzoic acid is reacted with thionyl chloride to give 2-methyl-4,5-di(methylsulfonyl)benzoyl chloride, and in stage e) 2-methyl-4,5-di(methylsulfonyl)benzoyl chloride is reacted with guanidinium chloride to give N-diaminomethylene-2-methyl-4,5-di(methylsulfonyl)benzamide.

Preferred oxidizing agents in stage c) are $H_2O_2$, $O_2$ or sodium perborate. Very particular preference is given to using sodium perborate.

The abbreviations used have the following meanings:

| | |
|---|---|
| n-Bu | n-butyl |
| Et | ethyl |
| Me | methyl |
| MTB | methyl tert-butyl |
| THF | tetrahydrofuran |
| h | hours |

In the above formulae, A is alkyl and has from 1 to 4, preferably 1, 2 or 3, carbon atoms. Alkyl is preferably methyl, also ethyl, propyl, isopropyl, butyl, isobutyl, sec-butyl or tert-butyl. Particular preference is given to methyl.

In the above formulae, the Cl substituent is preferably in the 3-, 4-, 5- or 6-position, particularly preferably in the 4-position relative to the position of the carboxyl group of the formula I.

The aryl bromides of the formula II are commercially available or can be prepared by methods known per se, as described, for example, in Houben-Weyl, Methoden der Organ. Chemie [Methods in Organic Chemistry].

$CO_2$ is used in solid or gaseous form.

The invention also provides a process, as described, characterized in that secondary organolithium compounds chosen from the group consisting of sec-butyllithium, isopropyllithium, sec-amyllithium, 4-heptyllithium, cyclopropyllithium or cyclohexyllithium or a tertiary organolithium compound chosen from the group consisting of tert-butyllithium, tert-amyllithium, triethyl-methyllithium, 1-methylcyclopentyllithium or adamantyllithium are used.

Preference is given to using secondary organolithium compounds chosen from the group consisting of sec-butyllithium, isopropyllithium, sec-amyllithium, 4-heptyllithium, cyclopropyllithium or cyclohexyllithium; particular preference is given to using sec-butyllithium.

The secondary or tertiary organolithium compounds listed above are commercially available or can be prepared by methods known per se, as described, for example, in Houben-Weyl, Methoden der Organ. Chemie [Methods in Organic Chemistry].

The invention also provides a process, as described, characterized in that the reaction is carried out at temperatures between −100° and +50° C. Preference is given to the temperature range between −50° and +40°, particular preference to the temperature range between −20° and +5° C., very particular preference to the temperature range between −15° and 0° C.

The invention also provides a process, as described, characterized in that the reaction product, following customary work-up of the reaction mixture, is precipitated using acid. Customary work-up means: NaOH (10%) is added to the reaction mixture, the phases are separated, the organic phase is washed with NaOH (10%), and the aqueous phases are extracted with the inert solvent and separated off. The acid is chosen from a group of acids which include organic acids, preferably formic acid, acetic acid or propionic acid, or inorganic acids, preferably sulfuric acid, nitric acid, hydrohalic acids such as hydrochloric acid or hydrobromic acid, or phosphoric acids such as orthophosphoric acid. Particular preference is given to using hydrochloric acid.

The invention also provides a process, as described, characterized in that the reaction is carried out in an inert solvent chosen from the group consisting of diethyl ether, MTB ether, THF, dioxane, toluene, hexane, petroleum ether or mixtures thereof. Particular preference is given to methyl tert-butyl ether.

The invention also provides a process, as described, characterized in that the aryl bromide of the formula II is introduced into an inert solvent chosen from the group consisting of diethyl ether, MTB ether, THF, dioxane, toluene, hexane, petroleum ether or mixtures thereof, particularly preferably MTB ether, the secondary or tertiary organolithium compound is added, this reaction mixture is added dropwise to a preferred volume of $CO_2$-saturated solvent and the mixture is again saturated with $CO_2$.

According to the process of the invention, the yields of ortho-alkylated benzoic acid derivatives of the formula I are generally between 30% and 90% when secondary or tertiary organolithium compounds are used, between 50% and 90% when secondary organolithium compounds are used, in particular between 70% and 90% when sec-butyllithium is used. Laborious purification steps by, for example, repeated recrystallization can be omitted. All temperatures above and below are given in ° C. The contents were determined, for example, after drying the crystals at 55°.

The invention also provides for the use of 4-chloro-2-methylbenzoic acid, prepared by the process described above, as intermediate in the synthesis of N-diaminomethylene-2-methyl-4-(1-pyrrolyl)-5-methylsulfonylbenzamide, known from EP 0 699 666 A1. Other intermediates of this synthesis sequence of N-diaminomethylene-2-methyl-4-(1-pyrrolyl)-5-methylsulfonylbenzamide, starting from the intermediate 4-chloro-2-methylbenzoic acid, are 2-methyl-4-chloro-5-methylsulfonylbenzoic acid, methyl 2-methyl-4-chloro-5-methylsulfonylbenzoate and methyl 2-methyl-4-(1-pyrrolyl)-5-methylsulfonylbenzoate.

Accordingly, the invention also provides a process for the preparation of N-diaminomethylene-2-methyl-4-(1-pyrrolyl)-5-methylsulfonylbenzamine, characterized in that in the first stage a) according to the invention 2-bromo-5-chlorotoluene is reacted with a secondary or tertiary organolithium compound, particularly preferably sec-butyllithium, and $CO_2$ to give the first intermediate 4-chloro-2-methylbenzoic acid, in stage b) a methylsulfonyl group is introduced by reacting 4-chloro-2-methylbenzoic acid with chlorosulfonic acid, sodium sulfite and methyl iodide to give the corresponding intermediate 2-methyl-4-chloro-5-methylsulfonylbenzoic acid, in stage c) the chlorine substituent is converted into a benzylamino group by reacting 2-methyl-4-chloro-5-methylsulfonylbenzoic acid with benzylamine to give the corresponding intermediate 4-benzylamino-5-methylsulfonyl-2-methylbenzoic acid, in stage d) the free acid from stage c) is esterified with an alcohol, in particular methanol, and the corresponding intermediate 4-benzylamino-5-methylsulfonyl-2-methylbenzoate is obtained, in stage e) the benzyl protective group is cleaved off by reduction to give the corresponding intermediate 4-amino-5-methylsulfonyl-2-methylbenzoate, in stage f) the pyrrole group is introduced by reacting 4-amino-5-methylsulfonyl-2-methylbenzoate with dimethoxytetrahydrofuran and, correspondingly, the intermediate 2-methyl-4-(1-pyrrolyl)-5-methylsulfonylbenzoate is obtained and finally, as described in EP 0 699 666 (p. 8, line 19 to p. 10, line 1), in stage g) by reaction of methyl 2-methyl-4-(1-pyrrolyl)-5-methylsulfonylbenzoate with guanidine to give the end-product N-diaminomethylene-2-methyl-4-(1-pyrrolyl)-5-methylsulfonylbenzamide, the guanidino group is introduced.

The invention also provides for the use of 4-chloro-2-methylbenzoic acid, prepared by the process described above, as intermediate in the synthesis of N-diaminomethylene-2-methyl-4,5-di(methylsulfonyl)benzamide, known from EP 0 758 644 A1. Other intermediates of this synthesis sequence of N-diaminomethylene-2-methyl-4,5-di(methylsulfonyl)benzamide, starting from the intermediate 4-chloro-2-methylbenzoic acid, are 2-methyl-4-chloro-5-methylsulfonylbenzoic acid, 2-methyl-4,5-di(methylsulfonyl)benzoic acid and 2-methyl-4,5-di(methylsulfonyl)benzoyl chloride.

Accordingly, the invention also provides a process for the preparation of N-diaminomethylene-2-methyl-4,5-di(methylsulfonyl)benzamine, characterized in that in the first stage a) according to the invention 2-bromo-5-chlorotoluene is reacted with a secondary or tertiary organolithium compound, particularly preferably sec-butyllithium, and $CO_2$ to give the first intermediate 4-chloro-2-methylbenzoic acid, in stage b) a methylsulfonyl group is introduced by reacting 4-chloro-2-methylbenzoic acid with chlorosulfonic acid, sodium sulfite and methyl iodide to give the corresponding intermediate 2-methyl-4-chloro-5-methylsulfonylbenzoic acid, in stage c) the chlorine substituent is converted into a second methylsulfonyl group by reacting 2-methyl-4-chloro-5-methylsulfonylbenzoic acid with sodium methylthiolate and then oxidizing the thioether with an oxidizing agent, in particular sodium perborate, to give the corresponding intermediate 2-methyl-4,5-di(methylsulfonyl)benzoic acid, in stage d) the free acid from stage c) is converted using thionyl chloride into the acid chloride 2-methyl-4,5-di(methylsulfonyl)benzoyl chloride as intermediate, and in stage e) finally, as described in EP 0 758 644 (p.9, lines 10–20), by reaction of 2-methyl-4,5-di(methylsulfonyl)benzoyl chloride with guanidinium chloride to give the end-product N-diaminomethylene-2-methyl-4,5-di(methylsulfonyl)benzamide, the guanidino group is introduced.

In the examples below and also in the above statements, the temperature is given in ° C. The pH corresponds to the base-ten logarithm of the $H^+$ ion concentration.

EXAMPLE 1

At a temperature of −18°, 728 ml of sec-butyllithium are added to a solution of 104.8 g of 2-bromo-5-chloro-toluene in 500 ml of MTB ether over the course of 30 min. The suspension is then added dropwise over the course of 20 min to 750 ml of $CO_2$-saturated MTB ether and saturated again for 15 min with gaseous $CO_2$. After a reaction time of 1 h at temperatures between −15° and −5°, 500 ml of NaOH (10%) are added, and the phases are separated. The organic phase is washed with 250 ml of NaOH (10%). The combined aqueous phases are extracted with 250 ml of MTB ether, adjusted to pH 1–2 with 250.4 g of HCl (37%) and cooled for 1 h at 5° in an ice/water bath. The crystals are washed with 2×50 ml of cold water and dried under reduced pressure at 55°. The yield of 4-chloro-2-methylbenzoic acid is 90%.

EXAMPLE 2

For comparison purposes, 2-bromo-5-chlorotoluene is reacted as in Example 1 with the lithiation reagents listed in Table I in the solvents given in Table I. The yield of 4-chloro-2-methylbenzoic acid is between 0 and 30%.

TABLE I

| Lithiation reagent | Solvent | Yield [%] |
| --- | --- | --- |
| MeLi | MTB ether | 0 |
| n-BuLi | MTB ether | 0 |
| n-BuLi | THF | 30 |

EXAMPLE 3

For comparison purposes, 2-bromo-5-chlorotoluene is reacted as in H. Gilman et al., J. Am. Chem. Soc. 1940, 62, 2327f with n-BuLi in boiling diethyl ether. The yield of 4-chloro-2-methylbenzoic acid is 20%.

EXAMPLE 4

20.5 g of 2-bromo-5-chlorotoluene dissolved in methyl tert-butyl ether are reacted as in Example 1 with 143 ml of tert-butyllithium and $CO_2$. The yield of 4-chloro-2-methylbenzoic acid is 32%.

EXAMPLE 5

Synthesis of N-diaminomethylene-2-methyl-4-(1-pyrrolyl)-5-methylsulfonylbenzamide a) At a temperature of -18°, 728 ml of sec-butyllithium are added to a solution of 104.8 g of 2-bromo-5-chlorotoluene in 500 ml of MTB ether over the course of 30 min. The suspension is then added dropwise over the course of 20 min to 750 ml of $CO_2$-saturated MTB ether and saturated again for 15 min with gaseous $CO_2$. After a reaction time of 1 h at temperatures between −15° and −5°, 500 ml of NaOH (10%) are added, and the phases are separated. The organic phase is washed with 250 ml of NaOH (10%). The combined aqueous phases are extracted with 250 ml of MTB ether, adjusted to pH 1–2 with 250.4 g of HCl (37%) and cooled for 1 h at 5° in an ice/water bath. The crystals are washed with 2×50 ml of cold water and dried under reduced pressure at 55°. The yield of 4-chloro-2-methylbenzoic acid is 90%.

b) 722 g of 4-chloro-2-methylbenzoic acid are dissolved in 2.4 l of chlorosulfonic acid at 15° with ice-cooling. After the solution has been heated to 110–115°, it is added dropwise to iced water (20 l) and then stirred. The precipitate is separated from the mother liquor, dried and then added to a suspension of 1333 g of sodium sulfite in 3 l of water. At the same time, the pH is maintained at pH 9 by addition of sodium hydroxide solution. After the suspension has been stirred at room temperature for four hours, the pH is adjusted to pH 1 using hydrochloric acid. The precipitate is separated from the mother liquor and suspended in 3 l of methanol and 2 l of water. 1.3 l of methyl iodide are added to this suspension, and the pH is adjusted to pH 9 using sodium hydroxide solution, and the mixture is heated to 40°. After methanol and excess methyl iodide have been distilled off, the mixture is diluted with water and extracted with ethyl acetate. Some of the ethyl acetate is distilled off, the solution which remains is adjusted to pH 1, and the solid which then forms is separated from the mother liquor and dried. This gives 2-methyl-4-chloro-5-methylsulfonylbenzoic acid in a yield of 67%.

c) A solution of 684 g of 2-methyl-4-chloro-5-methylsulfonylbenzoic acid and 884 g of benzylamine in 4 l of N-methylpyrrolidine is stirred for 8 h at 160°. The solution is then poured onto water, the pH is adjusted to pH 12 using sodium hydroxide solution and extracted with ethyl acetate. The aqueous phase is adjusted to pH 1 using hydrochloric acid. The precipitate which forms is filtered off and dried overnight. This gives 4-benzylamino-5-methylsulfonyl-2-methylbenzoic acid in a yield of 87%.

d) A suspension of 767 g of 4-benzylamino-5-methylsulfonyl-2-methylbenzoic acid in 12 l of methanol is heated to reflux. At the same time, HCl gas is introduced. When the reaction is complete, the clear solution is poured onto ice and the precipitate which forms is filtered off and dried. This gives methyl 4-benzylamino-5-methylsulfonyl-2-methylbenzoate in a yield of 96%.

e) 68 g of Pd-C (5%) are added to a solution of 683 g of methyl 4-benzylamino-5-methylsulfonyl-2-methylbenzoate in 6.8 l of methanol, and 48.4 l of hydrogen are introduced. After 4 h, the mixture is diluted with 5 l of methylene chloride, the catalyst is filtered off and some of the solvent is distilled off. The precipitate which forms is filtered off from the concentrated mother liquor and dried. This gives methyl 4-amino-5-methylsulfonyl-2-methylbenzoate in a yield of 98%.

f) 260 ml of dimethoxytetrahydrofuran and 23.8 g of 4-chloropyridinium chloride are added to a solution of 385.9 g of methyl 4-amino-5-methylsulfonyl-2-methylbenzoate in 6 l of 1,4-dioxane. The solution is refluxed until the reaction is complete, and the solvent is distilled off. The residue is taken up in ethyl acetate and washed with water and dried over $Na_2SO_4$. Then, the mixture is decolorized using 15 g of activated carbon under reflux, the activated carbon is filtered off and the ethyl acetate is distilled off. The residue which forms is recrystallized from methanol. This gives methyl 2-methyl-4-(1-pyrrolyl)-5-methylsulfonylbenzoate in a yield of 89%.

g) A solution of 694 g of guanidine and 310 g of methyl 2-methyl-4-(1-pyrrolyl)-5-methylsulfonylbenzoate in 3 l of methanol is stirred for 3 h at 50°. Then, water is added to the reaction mixture, and the crude product which forms as a result is filtered off and recrystallized from methanol. This gives N-diaminomethylene-2-methyl-4-(1-pyrrolyl)-5-methylsulfonylbenzamide in a yield of 66%.

EXAMPLE 6

Synthesis of N-diaminomethylene-2-methyl-4,5-di (methylsulfonyl)benzamide a) At a temperature of −18°, 728 ml of sec-butyllithium are added to a solution of 104.8 g of 2-bromo-5-chlorotoluene in 500 ml of MTB ether over the course of 30 min. The suspension is then added dropwise to 750 ml of $CO_2$-saturated MTB ether over the course of 20 min and saturated again for 15 min with gaseous $CO_2$. After a reaction time of 1 h at temperatures between −15° and −5° C., 500 ml of NaOH (10%) are added, and the phases are separated. The organic phase is washed with 250 ml of NaOH (10%). The combined aqueous phases are extracted with 250 ml of MTB ether, adjusted to pH 1–2 with 250.4 g of HCl (37%) and cooled for 1 h at 5° in an ice/water bath. The crystals are washed with 2×50 ml of cold water and dried under reduced pressure at 55°. The yield of 4-chloro-2-methylbenzoic acid is 90%.

b) 722 g of 4-chloro-2-methylbenzoic acid are dissolved in 2.4 l of chlorosulfonic acid at 150 with ice-cooling. After the solution has been heated to 110–115°0, it is added dropwise to iced water (20 l) and then stirred. The precipitate is separated from the mother liquor, dried and then added to a suspension of 1333 g of sodium sulfite in 3 l of water. At the same time, the pH is maintained at pH 9 by addition of sodium hydroxide solution. After the suspension has been stirred at room temperature for four hours, the pH is adjusted to pH 1 using hydrochloric acid. The precipitate is separated from the mother liquor and suspended in 3 l of methanol and 2 l of water. 1.3 l of methyl iodide are added to this suspension, and the pH is adjusted to pH 9 using sodium hydroxide solution, and the mixture is heated to 40°. After methanol and excess methyl iodide have been distilled off, the mixture is diluted with water and extracted with ethyl acetate. Some of the ethyl acetate is distilled off, the solution which remains is adjusted to pH 1, and the solid which then forms is separated from the mother liquor and dried. This gives 2-methyl-4-chloro-5-methylsulfonylbenzoic acid in a yield of 67%.

c) 360 g of sodium methylthiolate are added to a solution of 600 g of 2-methyl-4-chloro-5-methylsulfonylbenzoic acid in 4 l of DMF, and the mixture is stirred at 130° until the reaction is complete. The mixture is then poured onto iced water and the pH is adjusted to pH 1 using hydrochloric acid. The precipitate which forms is filtered off and dried to give 5-methylsulfonyl-2-methyl-4-methylsulfanylbenzoic acid in a yield of 86%. 73 g of 5-methylsulfonyl-2-methyl-4-methylsulfanylbenzoic acid are then dissolved in 1 l of glacial acetic acid, and 180 g of sodium perborate are added. The reaction mixture is heated for 1 h at an internal temperature of 65°. Most of the glacial acetic acid is distilled off and the residue which remains is triturated with ethyl acetate. The precipitate which forms is filtered off and washed several times with a 1:1 mixture of ethyl acetate and diethyl ether. To remove the boric acid, the precipitate is stirred in 1 n hydrochloric acid, then filtered off and dried. This gives 2-methyl-4,5-di(methylsulfonyl)benzoic acid in a yield of 50%.

d) 400 ml of thionyl chloride are added to 41 g of 2-methyl-4,5-di(methylsulfonyl)benzoic acid, and the mixture is refluxed until the reaction is complete. The excess thionyl chloride is distilled off and codistilled several times with toluene. This gives 2-methyl-4,5-di(methylsulfonyl) benzoyl chloride in a yield of 98%.

e) 128.4 g of guanidinium chloride are added to a solution of 38.5 g of sodium in 1.3 l of methanol, and the mixture is stirred for 30 minutes at room temperature and filtered. After the solvent has been removed and the mixture has been washed with toluene, the residue is taken up in 1.3 l of ethylene glycol monomethyl ether and added to a solution of 42.8 g of 2-methyl-4,5-di(methylsulfonyl)benzoyl chloride in 1.7 l of ethylene glycol monomethyl ether. The mixture is stirred for 2 h at room temperature and diluted with iced water, and 1 n hydrochloric acid is added. Then, the mixture is washed with ethyl acetate and adjusted to a pH of pH 9. Customary work-up and removal of the solvent gives, after recrystallization from diethyl ether, the N-diaminomethylene-2-methyl-4,5-di(methylsulfonyl) benzamide in a yield of 44%.

What is claimed is:

1. A process for the preparation of N-diaminomethylene-2-methyl-4,5-di(methylsulfonyl)benzamide, wherein a) 2-bromo-5-chlorotoluene is reacted with a secondary or tertiary organolithium compound and $CO_2$ to produce 4-chloro-2-methylbenzoic acid, b) 4-chloro-2-methylbenzoic acid is reacted with chlorosulfonic acid, sodium sulfite and methyl iodide to produce 2-methyl-4-chloro-5-methylsulfonylbenzoic acid, c) 2-methyl-4-chloro-5-methylsulfonylbenzoic acid is reacted with sodium methylthiolate and then oxidized with an oxidizing agent to produce 2-methyl-4,5-di (methylsulfonyl)benzoic acid, d) 2-methyl-4,5-di(methylsulfonyl)benzoic acid is reacted with thionyl chloride to produce 2-methyl-4,5-di (methylsulfonyl)benzoyl chloride, and e) 2-methyl-4,5-di(methylsulfonyl)benzoyl chloride is reacted with guanidinium chloride to produce N-diaminomethylene-2-methyl-4,5-di(methylsulfonyl) benzamide.

2. A process according to claim 1, wherein the tertiary organolithium compound is sec-butyllithium.

3. In a process for preparing N-diaminomethylene-2-methyl-4,5-di(methylsulfonyl)benzamide, the step comprising reacting 2-bromo-5-chlorotoluene with a secondary or tertiary organolithium compound and $CO_2$ to produce 4-chloro-2-methylbenzoic acid.

* * * * *